(12) United States Patent
Kim et al.

(10) Patent No.: US 11,241,172 B2
(45) Date of Patent: Feb. 8, 2022

(54) ULTRASONIC DIAGNOSTIC APPARATUS AND METHOD OF CONTROLLING THE SAME

(71) Applicant: SAMSUNG MEDISON CO., LTD., Gangwon-do (KR)

(72) Inventors: Dae Young Kim, Seoul (KR); Chan Mo Kim, Seoul (KR); Tae-Heon Roh, Gwangmyeong-si (KR)

(73) Assignee: SAMSUNG MEDISON CO., LTD., Gangwon-do (KR)

( * ) Notice: Subject to any disclaimer, the term of this patent is extended or adjusted under 35 U.S.C. 154(b) by 246 days.

(21) Appl. No.: 16/075,361

(22) PCT Filed: Feb. 2, 2017

(86) PCT No.: PCT/KR2017/001132
§ 371 (c)(1),
(2) Date: Aug. 3, 2018

(87) PCT Pub. No.: WO2017/135698
PCT Pub. Date: Aug. 10, 2017

(65) Prior Publication Data
US 2019/0038182 A1     Feb. 7, 2019

(30) Foreign Application Priority Data

Feb. 5, 2016   (KR) ................. 10-2016-0014600

(51) Int. Cl.
*A61B 8/12*          (2006.01)
*A61B 5/11*          (2006.01)
(Continued)

(52) U.S. Cl.
CPC .......... *A61B 5/1107* (2013.01); *A61B 5/1121* (2013.01); *A61B 5/459* (2013.01);
(Continued)

(58) Field of Classification Search
CPC .......... A61B 2562/0219; A61B 5/1107; A61B 5/1121; A61B 5/459; A61B 5/681;
(Continued)

(56) References Cited

U.S. PATENT DOCUMENTS

2012/0316407 A1   12/2012  Anthony et al.
2015/0045693 A1    2/2015  Otsamo et al.

FOREIGN PATENT DOCUMENTS

CN       103126657 A    6/2013
JP       2006-020749 A  1/2006
KR   10-2016-0012664 A  2/2016

OTHER PUBLICATIONS

Written Opinion and International Search Report dated Apr. 27, 2014 (with English translation).

*Primary Examiner* — Mark D Remaly
(74) *Attorney, Agent, or Firm* — Morgan, Lewis & Bockius LLP (57) ABSTRACT

Disclosed is a ultrasonic diagnostic apparatus an a method of controlling the same, capable of allowing a sonographer to take an appropriate rest by measuring the usage time and the angle of bend of the probe and assigning weights to the usage time and the angle of bend of the probe such that the wrist fatigue of a sonographer is determined, and warning the sonographer about the determined wrist fatigue, the ultrasonic diagnostic apparatus including a probe configured to transmit an ultrasonic signal to a target object and receive a ultrasonic signal reflected from the target object; a storage configured to store a weight that is determined on the basis of a type of the probe and an application of the probe; and a controller configured to determine a wrist fatigue of a user who uses the probe on the basis of the stored weight and a usage time of the probe.

13 Claims, 10 Drawing Sheets

(51) Int. Cl.
*A61B 8/00* (2006.01)
*A61B 5/00* (2006.01)
*A61B 8/08* (2006.01)

(52) U.S. Cl.
CPC ............ *A61B 5/681* (2013.01); *A61B 5/6824* (2013.01); *A61B 5/7275* (2013.01); *A61B 5/746* (2013.01); *A61B 8/4405* (2013.01); *A61B 8/4411* (2013.01); *A61B 8/52* (2013.01); *A61B 8/54* (2013.01); *A61B 8/42* (2013.01); *A61B 8/4438* (2013.01); *A61B 8/4488* (2013.01); *A61B 2562/0219* (2013.01)

(58) Field of Classification Search
CPC ..... A61B 5/6824; A61B 5/7275; A61B 5/746; A61B 8/42; A61B 8/4405; A61B 8/4411; A61B 8/4438; A61B 8/4488; A61B 8/52; A61B 8/54; G16H 50/30
See application file for complete search history.

| Phased array(200g) | | Convex Probe A(400g) | | Convex Probe B(450g) | |
|---|---|---|---|---|---|
| Application | Weight | Application | Weight | Application | Weight |
| Abdomen | 1 | Abdomen | 1.5 | Abdomen | 1.6 |
| Cardiac | 0.9 | OB | 1.5 | OB | 1.6 |

| ANGLE OF BEND($\theta$) | WEIGHT |
|---|---|
| 0~10 | 1 |
| 11~20 | 1.2 |
| 21~30 | 1.3 |
| 31~40 | 1.4 |
| 41~50 | 1.5 |

FIG. 10

ULTRASONIC DIAGNOSTIC APPARATUS AND METHOD OF CONTROLLING THE SAME

CROSS REFERENCE

This patent application is the U.S. National Phase under 35 U.S.C. 371 of International Application No. PCT/KR2017/001132, filed on Feb. 2, 2017, which claims the benefit of Korean Patent Application No. 10-2016-0014600, filed on Feb. 5, 2016, the entire contents of each are hereby incorporated by reference.

TECHNICAL FIELD

The present disclosure relates to an ultrasonic diagnostic apparatus and a method of controlling the same, and more specifically, to an apparatus for determining a wrist fatigue using a probe and a method of controlling the same.

BACKGROUND ART

An ultrasonic diagnostic apparatus irradiates an ultrasonic signal from the skin of the body of a target object toward a desired portion within the body, and obtains an image regarding a tomogram of soft tissue or a bloodstream using the reflected ultrasonic signal (ultrasonic echo signal).

The ultrasonic diagnostic apparatus has a small size, is inexpensive, displays an image in real time, and does not cause X-ray exposure, as compared to an X-ray diagnostic apparatus, a computerized tomography (CT) scanner, a magnetic resonance imager (MRI) and a nuclear medicine diagnostic apparatus, thus having high safety. Therefore, the ultrasonic diagnostic apparatus is widely used for diagnoses of the heart and the abdomen and urinary and maternity diagnoses.

The ultrasonic diagnostic devices provide benefits to perform real-time scanning. Real-time scanning provides real-time interactivity and visual feedback, and rapidly generates an image such that a sonographer scans a target object or identifies a motion inside the body, such as a blood flow.

For the real-time scanning, the ultrasonic diagnostic apparatus employs a probe. A probe is an apparatus that transmits ultrasonic waves to a target object and receives echo ultrasonic waves from the target object and converts the received echo ultrasonic waves into electrical signals. The probes are provided in a small size that fits the hand of a sonographer and in a lightweight for a sonographer to easily shift the object of interest.

Such a probe allows a sonographer to examine and correct structures of interest, thereby improving both the quality of diagnosis and patient throughput.

Meanwhile, the sonographer uses the probe for a long time, and often needs to change the position of the probe to correct the structure of interest. In addition, depending on the object of interest, a case in which the probe is strongly pressed to come into close contact with the object of interest exists. This may lead to a load to the wrist joint of the sonographer, often causing a tunnel syndrome.

DISCLOSURE

Technical Problem

Therefore, it is an object of the present disclosure to provide an ultrasonic diagnostic apparatus capable of allowing a sonographer to take an appropriate rest by measuring the usage time and the angle of bend of the probe and applying weights to the usage time and the angle of bend of the probe to determine the wrist fatigue of a sonographer, and warning the sonographer about the wrist fatigue.

Technical Solution

Therefore, it is an aspect of the present disclosure to provide an ultrasonic diagnostic apparatus including: a probe configured to transmit an ultrasonic signal to a target object and receive an ultrasonic signal reflected from the target object; a storage configured to store a weight that is determined on the basis of a type of the probe and an application of the probe; and a controller configured to determine a wrist fatigue of a user who uses the probe on the basis of the stored weight and a usage time of the probe.

The controller may determine the wrist fatigue by storing the usage time to which the weight is assigned, and summating the stored usage times.

The probe may transmit information regarding the usage time to the controller on the basis of an input command of the user.

The ultrasonic diagnostic apparatus may further include an output including at least one of a display, a speaker, and a warning lamp.

The probe may warn the user through vibration.

The controller may control the output or the probe on the basis of the wrist fatigue such that a warning is output.

The controller may control the probe and receives information regarding the usage time through wireless communication.

Therefore, it is another aspect of the present disclosure to provide an ultrasonic diagnostic apparatus including: a probe including a motion sensor; a storage configured to store a weight that is determined on the basis of a type of the probe and an application of the probe; and a controller configured to measure an angle of bend of the probe through the motion sensor, and determine a wrist fatigue of a user on the basis of the stored weight, a usage time of the probe, and the angle of bend of the probe.

The controller may determine the wrist fatigue by determining the weights for sections based on the measured angle of bend, store the usage times with the weights assigned, and summate the usage times.

The ultrasonic diagnostic apparatus may further include an output including at least one of a display, a speaker, and a warning lamp The probe may warn the user through vibration.

The controller may control the output or the probe on the basis of the wrist fatigue such that the user is warned.

The controller may control the probe and receive data regarding the usage time and the angle of bend through wireless communication.

The controller may measure the angle of bend of the probe by comparing a motion sensor coupled to a wearable device with the motion sensor of the probe.

The controller may determine that the probe is used when radio wave signals of the wearable device and the probe have a strength equal to or greater than a threshold value.

Advantageous Effects

As is apparent from the above, the ultrasonic diagnostic apparatus and the method of controlling the same according to the present disclosure can allow a sonographer to take an appropriate rest by measuring the usage time and the angle of bend of the probe and applying weights to the usage time and the angle of bend of the probe to determine the wrist fatigue of a sonographer, and warning the sonographer about the determined wrist fatigue.

BEST MODE

Advantages and features of exemplary embodiments, and methods of achieving the same will be clearly understood with reference to the accompanying drawings and the following detailed exemplary embodiments.

The present inventive concept is not limited to exemplary embodiments described herein, but may be implemented in various different forms.

A terminology "a target object" used herein may refer to a person or animal, or a part of person or animal. For example, the target object may include organs, such as a liver, a heart, a uterus, a brain, a breast and abdomen, or a blood vessel. Also, a terminology "a user" may refer to a sonographer, a physician, a nurse, a clinical pathologist, a medical imaging expert, or the like, and also refer to a technician repairing a medical device, but the scope of the user is not limited thereto.

A terminology "an ultrasonic image" used throughout the specification refers to an image of a target object obtained by using ultrasonic, and further refer to an image obtained using an X-ray diagnostic apparatus, a computerized tomography (CT) scanner, a magnetic resonance imager (MRI), and a nuclear medicine diagnosis device.

In addition, the technology of an ultrasonic imaging apparatus and a method of controlling the same may be used for a diagnostic apparatus, and the use may expand to X-ray imaging apparatus, an X-ray fluoroscopy apparatus, a CT scanner, a magnetic resonance imager (MRI), a positron emission tomography apparatus, and an ultrasonic imaging apparatus. The disclosed embodiments illustrate an ultrasonic imaging apparatus as an example, but the present disclosure is not limited thereto.

The term "include (or including)" or "comprise (or comprising)" is inclusive or open-ended and does not exclude additional, unrecited elements or method steps, unless otherwise mentioned. The terms as used throughout the specification, such as "~part", "~module", "~member", "~block", etc., may be implemented in software and/or hardware, and a plurality of "~parts", "~modules", "~members", or "~blocks" may be implemented in a single element, or a single "~part", "~module", "~member", or "~block" may include a plurality of elements.

Hereinafter, embodiments will be described in detail with reference to the accompanying drawings.

Figure 1:
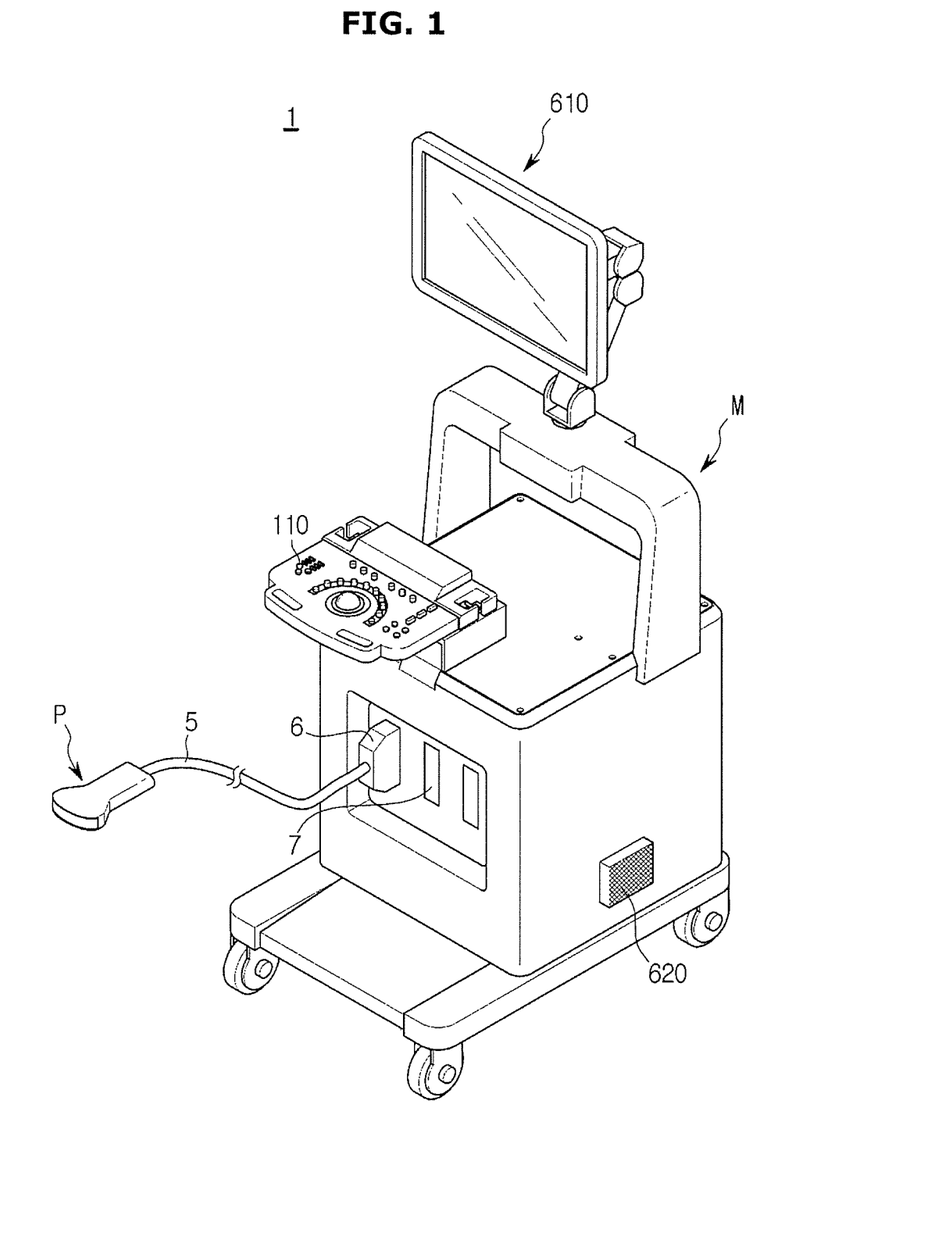
FIG. 1 is a diagram illustrating the external appearance of an ultrasonic diagnostic apparatus according to an embodiment.
Figure 2:
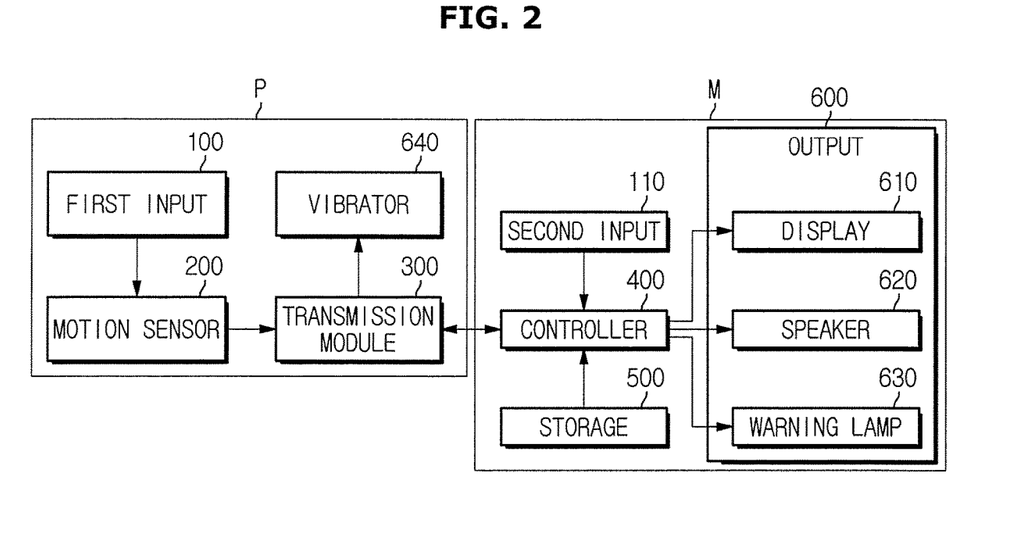
FIG. 2 is a control block diagram illustrating an ultrasonic diagnostic apparatus according to an embodiment.
Figure 3:
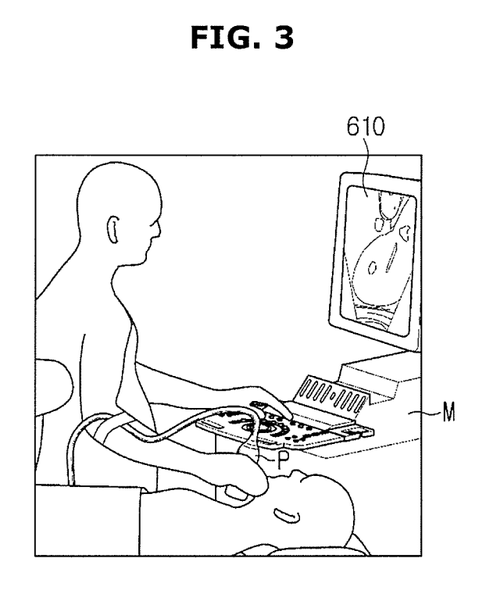
FIG. 3 is a diagram illustrating an example in which a user uses a probe.

FIG. 1 is a diagram illustrating the external appearance of an ultrasonic diagnostic apparatus according to an embodiment, FIG. 2 is a control block diagram illustrating an ultrasonic diagnostic apparatus according to an embodiment, and FIG. 3 is a diagram illustrating an example in which a user uses a probe.

Referring to FIG. 1, an ultrasonic diagnostic apparatus 1 includes: an ultrasonic probe P that transmits an ultrasonic wave to a target object, receives an echo ultrasonic wave from the target object, and converts the received ultrasonic wave into an electric signal; and a main body M connected to the ultrasonic probe P and including a second input 110 and a display 610 that displays an ultrasonic image.

The ultrasonic probe P is connected to the main body M of the ultrasonic diagnostic apparatus through a cable 5 to receive various signals required for controlling the ultrasonic probe P or may transmit an analog signal or digital signal corresponding to an ultrasonic eco signal received by the ultrasonic probe P to the main body M.

To this end, one end of the cable 5 is connected to the ultrasonic probe P and the other end of the cable 5 is provided with a connector 6 which may be coupled to or separated from a slot 7 of the main body M.

The implementation of the ultrasonic probe P is not limited thereto, and the ultrasonic probe P may be implemented as a wireless probe to exchange signals with the main body M through a network formed between the ultrasonic probe P and the main body M.

The main body M and the ultrasonic probe P may exchange control commands and data using the cable 5. For example, when a user inputs information regarding a focal depth, a size or shape of an aperture, or a steering angle through the second input 110, the information may be transmitted to the ultrasonic probe P through the cable 5 and used for transmission/reception beamforming.

When the ultrasonic probe P is implemented as a wireless probe as described above, the ultrasonic probe P is connected to the main body M via a wireless network rather than the cable 5. Even when the ultrasonic probe P is connected to the main body M through the wireless network, the main body M and the ultrasonic probe P may exchange control commands and data as described above.

The control commands or data exchanged between the ultrasonic probe P and the main body M may include various types of command or data. As an example of the present disclosure, the ultrasonic probe P may not only serves to transmit an image of a target object obtained through transmission/reception beamforming (i.e., a basic function) but also serves to transmit data regarding a usage time of a user. Details thereof will be described later with reference to FIG. 2.

On the other hand, the main body M that has received the data transmitted via the cable 5 may analyze the data, and transmit a result of analysis of the data to a user through the display 610 or a speaker 620.

Referring to FIG. 2, the main body M may include the second input 110, a controller 400, a storage 500, and an output 600.

The controller 400 controls the overall operation of the ultrasonic diagnostic apparatus 1. In detail, the controller 400 controls operations of the respective components of the ultrasonic diagnostic apparatus 1, that is, the second input 110, the storage 500, and the output 600.

In detail, the controller 400 may perform a basic function of the ultrasonic diagnostic apparatus 1, such as receiving data regarding a target object obtained through beamforming, generating an image on the basis of the received data, and reproducing the image through the display 610.

In addition, the controller 400 may receive data regarding a usage time for which a user uses the probe P and may store the data in the storage 500. That is, the controller 400 may determine a wrist fatigue of the user on the basis of information about the type of the probe P connected to the main body M and an application for which the probe P is used, which is stored in the storage 500, and may control the output 600 to warn the user when the wrist fatigue is equal to or higher than a predetermined grade.

In addition, the controller 400 may receive an input of the user through the second input 110 and process a command corresponding to the input. That is, the second input 110 may switch a diagnostic mode or distinguish the applications for the user to efficiently photograph the target object.

In this case, the application refers to software executed in an operating system, in detail, an application indicating an object or a portion of the object, abdomen, cardiac and obstetric, for which the probe P is used to capture an image.

In detail, when the user uses the probe P to photograph the abdomen, a pressure greater than that applied in photographing the cardiac is required. In this case, the user inputs a selection of an application corresponding to the target object currently to be photographed through the second input 110, and the controller 400 may determine the fatigue on the basis of the application.

Meanwhile, the second input 110 may be implemented using various devices by which a user may input data, instructions, or commands, for example, a keyboard, a mouse, a trackball, a tablet PC, or a touch screen module.

The storage 500 is configured to store a usage time for which the user uses the probe P, a lookup data in which weights for a probe P and an application of the probe P are stored, a sampling period required for motion sensing, an angle of bend of a probe P, and the like. Data stored in the storage 500 may be described in detail with reference to FIG. 4.

The storage 500 may implemented in a type of at least one of flash memory type, hard disk type, multimedia card micro type, card type memory (e.g., SD or XD memory), Random Access Memory (RAM), Static Random Access Memory (SRAM), Read-Only Memory (ROM), Electrically Erasable Programmable Read-Only Memory (EEPROM), Programmable Read-Only Memory (PROM), magnetic memory, magnetic disk, and optical disk. However, the storage is not limited thereto, and may be implemented in any other form generally known in the art.

The output 600 serves to warn a user when the wrist fatigue determined by the controller 400 exceeds a reference value. In detail, the output 600 may warn the user that the wrist fatigue is accumulated through the display 610, the speaker 620, and the warning lamp 630.

In more detail, the display 610 may output the extent of a wrist fatigue on a screen visible to the user as a numerical value or a warning indication icon.

In addition, the display 610 may display a menu and guide required for ultrasonic diagnosis, and an ultrasonic image acquired in the ultrasonic diagnostic process. That is, the display 610 may display an ultrasonic image of a target site inside the target object, which is generated by the controller 400. The ultrasonic image displayed on the display 610 may be an A-mode ultrasonic image, a B-mode ultrasonic image, or a 3D ultrasonic image.

Meanwhile, the display 610 may be implemented using various forms of displays generally known in the art, such as a cathode ray tube (CRT) and a liquid crystal display (LCD).

The speaker 620 may output a guide speech or warning sound indicating an increase in the wrist fatigue. The position of the speaker 620 shown in FIG. 1 is only one example of the present disclosure, and the speaker may be implemented in various forms and positions.

In addition, a warning lamp, such as a light emitting diode (LED), may be installed on a part of the main body M, and the warning lamp 630 may be turned on to warn the user.

The output device of the output 600 described above is merely an example of the present disclosure, and thus may be provided in various forms without limitation. That is, the output 600 may be not limited and be provided using various devices or modules as long as it can warn the user about the danger of a serve wrist fatigue.

Referring to FIG. 3, a user photographs a neck portion of the target object using the probe P. The display 610 shown in FIG. 3 displays an ultrasonic image of a current target object.

Here, the user holds the probe P and changes the position of the probe P using the wrist. In this case, the ultrasonic diagnostic apparatus 1 collects data regarding use of the wrist from the probe P. The controller 400 may determine the wrist fatigue on the basis of the collected data and warn the user about the wrist fatigue.

On the other hand, the probe P needs to acquire information regarding use of the wrist of the user.

Referring again to FIG. 2, the probe P may include a first input 100, a motion sensor 200, a transmission module 300, and a vibrator 640.

The first input 100 serves to acquire data indicating that the user is using the probe P as described above. That is, the user may transmit to the controller 400 information that the probe P is being used by the user through the first input 100 while using the probe P.

The first input 100 may include a button, a touch sensor, and the like, and may be implemented using any other devices as long as it can receive a command indicating that the probe P starts being used.

The motion sensor 200 is a component for determining the angle of bend of the users wrist while the probe P is being used. The motion sensor 200 may be a gyro sensor.

A gyro sensor is a sensor that measures the change in azimuth of an object, on the basis of the characteristic in which an initially set direction is kept constant with a high accuracy regardless of the rotation of the earth.

In the present disclosure, the gyro sensor may sense an angular velocity indicating the degree to which an angle changes with respect to the X, Y, and Z axes, that is, the angle of bend, and may measure the angle of turn of the probe P with respect to a reference direction, for example, the gravity direction.

That is, the motion sensor 200 including the gyro sensor may measure the degree of bend of the probe P. This allows a user to estimate the degree to which the wrist is used while using the probe (P).

To summarize, the probe P collects information regarding use of the probe P by the user, that is, a usage time, through the first input 100, and collects information regarding the angle of bend of the wrist while the user is using the probe P through the motion sensor 200.

Meanwhile, the transmission module 300 converts the measured information into an electrical signal, and transmits the electrical signal to the main body M through the cable 5 as shown in FIG. 1 or through a wireless signal. That is, the transmission module 300 serves to transmit the information collected by the probe P to the controller 400.

In addition, the transmission module 300 may receive a command from the controller 400. For example, the controller 400 may control the vibrator 640 through the transmission module 300 to generate vibration in the probe P held by the user.

In detail, the vibrator 640 may include haptic technology. Haptic technology refers to a technology that allows a user to feel a sense of touch by generating vibration, force, or impact in the device.

That is, when it is determined that a user needs to be warned about a wrist fatigue, the controller 400 controls not only the output 600 but also the vibrator 640 through the transmission module 300 such that the user is warned of the wrist fatigue through a sense of touch.

According to an embodiment of the present disclosure, the probe P and the main body M may be connected through wireless communication. In this case, the transmission module 300 may convert the measured usage time and image information into a communication signal, and transmit the converted communication signal to the controller 400.

In addition, the transmission module 300 according to another embodiment of the present disclosure may exchange a radio frequency (RF) signal with a wearable device, and thus the controller 400 may determine that the probe P is being used when the signal transmitted and received between the probe P and the wearable device is higher than or equal to a threshold value.

The wearable device refers to a device, such as glasses, a wristwatch, or a band-type device that may wirelessly interoperates with a smartphone or a tablet. The wearable device may be implemented in any other device as long as it can be worn on a user's wrist and coupled to a motion sensor that is required for measuring the bending of the wrist using the probe (P). An embodiment related to the wearable device will be described later with reference to FIG. 10.

The components and modules described with reference to FIGS. 1 and 2 are merely examples of the present disclosure, and various modifications to the measurement of the wrist fatigue using the probe P may be possible.

Figure 4:
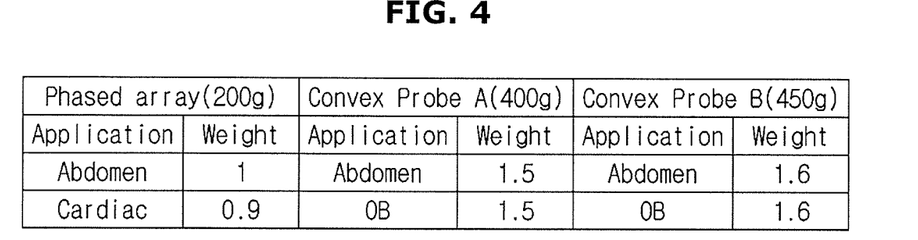
FIG. 4 is a table showing types and applications of a probe according to an example.
Figure 5:
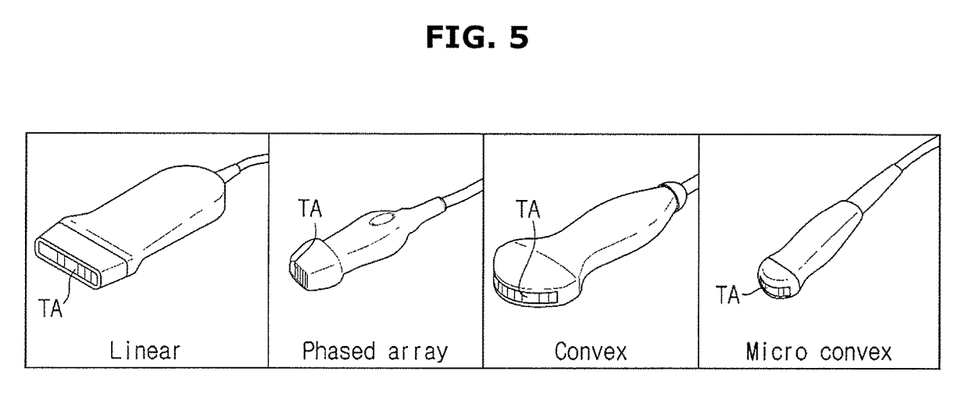
FIG. 5 is a diagram for describing the types of a probe according to an example.

FIG. 4 is a table showing types and applications of a probe according to an example. FIG. 5 is a diagram for describing the types of a probe according to an example. In order to avoid redundancy, the following description will be made with reference to both FIGS. 4A and 4B.

As described above, the controller 400 determines the wrist fatigue by assigning different weights according to the types and applications of the probe.

Referring to FIG. 4, Phase array, Convex Probe A, and Convex Probe B described in the first column of the table represent the types of probes (P). The second column includes items describing the applications of the probe P and weights thereof.

The types of the probe P will be described in conjunction with FIG. 5.

In general, a probe P includes a transducer array TA. The ultrasonic transducer array TA refers to an array in which a plurality of ultrasonic transducer elements are arranged.

The ultrasonic transducer array TA is vibrated by a pulse signal or an alternating current applied thereto to generate ultrasonic waves, and the ultrasonic waves generated in the ultrasonic transducer array TA are reflected by at least one target side inside a target object and returned to the ultrasonic transducer array TA again. The ultrasonic transducer array TA receives ultrasonic waves reflected from the at least one target site, that is, eco-ultrasonic waves.

As such, the transducer array (TA) is required for the ultrasonic probe (P) to perform a basic function. Accordingly, the probe P may take various forms according to the types on the basis of the transducer array TA.

In detail, the probe P is divided on the basis of the shape of the transducer array. A probe P having a linear arrangement of transducers is referred to as an array transducer.

Generally, in the case of 1-D (1-Dimensional), the transducer is provided in an array, and may be classified into three types of transducers: a linear array transducer, a convex array transducer, and a phased array transducer.

Convex probe is referred to a convex type probes P and takes a form having benefits of a linear probe P and a sector probe P. The convex probe P having a convex surface produces a fan-shaped image and thus is mainly used for examining a wide area, such as the abdomen.

Micro Convex Probe refers to a probe P that provides the same performance as that of Convex Probe and has transducers designed in a small size suitable for examining a narrow area.

In addition to the probes shown in FIG. 5, the present disclosure may include various types of a probe, and different weights may be assigned according to the types of a probe.

Referring again to FIG. 4, the table shows an example in which different weights are assigned according to the types and the loads of the probe P.

In detail, Phased Array (200 g) represents a probe P including a rectangular shape transducer and having a load of 200 g. Convex Probe A (400 g) and Convex Probe B (450 g) represent convex probes (P) that are distinguished according to the loads, that is, distinguished as a small probe P and a medium probe P.

In the table, it can be seen that Phased Array (200 g) is assigned different weights according to the applications, but is assigned a weight smaller than those of Convex Probe A (400 g) and Convex Probe B (450 g). Such a weighting is based on the assumption that there is a probe type that puts small burden on the wrist of the user, and the load of a probe is greatly influenced by the type of a transducer. The type exerts an influence on the load applied is given a small amount of burden according to the type of the probe P, and the load is highly influenced by the type of the transducer.

On the other hand, the numerical values shown in FIG. 4 are merely an example of the present disclosure, and the weights assigned according to the applications may be vary.

Different applications of the probe P may be provided for different regions of a target object that are diagnosed by a user through the probe P. Referring to the table, Phased Array (200 g) is assigned a weight of 1 in the case of an application of Abdomen, and is assigned a weight of 0.9 in the case of an application of Cardiac. This is because the degree of a force applied by the user to the probe P differs depending on the region of the target object.

Convex Probe A (400 g) is assigned a weight of 1.5 in the case of an application of abdomen, and is assigned a weight of 1.5 in the case of a fetus measurement (OB).

The controller 400 may predict the wrist fatigue of the user by assigning different weights according to the probes P and the applications thereof using the look-up table shown in FIG. 4. On the other hand, such a look-up table may be stored in the storage 500

Figure 6:
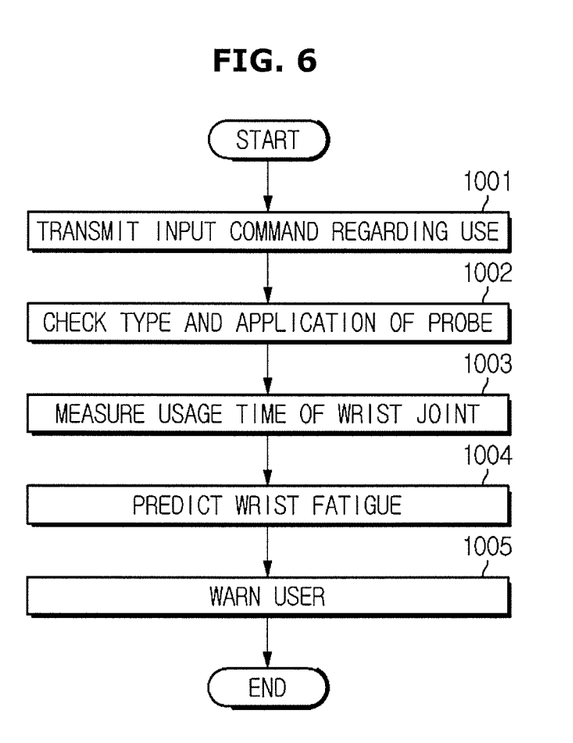
FIG. 6 is a flowchart showing an operation of determining a wrist fatigue of a user according to an example.

FIG. 6 is a flowchart showing an operation of determining a wrist fatigue of a user according to an example.

Referring to FIG. 6, the controller 400 according to an example measures a time for which the user uses the probe P and determines the wrist fatigue on the basis of the measured time.

In detail, the user inputs an input command to the first input 100 of the probe P, and the user uses the probe P (1001).

As described above, the first input 100 of the probe P may be provided in the form of a button or a touch sensor. In addition, when the first input 100 is omitted in the probe P, an input command indicating that the probe P is used may be transmitted through the second input 110 of the main body M.

The controller 400 receives an electrical signal indicating that the user uses the probe P from the transmission module 300, and may measure the usage time from the point of time at which the electric signal is received.

Then, the controller 400 checks the type and application of the probe P (1002).

As described above, the types and applications of the probe P may be provided in variety, and are used as a basis for assigning different weights as shown in FIG. 4.

When the user changes the probe P or the application, the controller 400 may store the time at which the user changes the probe P or the application in the storage 500, and may measure a usage time of the probe P in connection with the change.

The controller 400 continuously measures the usage time of the probe P (1003). The measurement may be provided in various forms according to a user's input, and the usage time may vary according to a user's input. The controller 400 may measure the usage time by adding up previous usage times using the storage 500 at predetermined time intervals.

The controller 400 determines the wrist fatigue (1004).

The wrist fatigue is determined on the basis of the usage time of the probe P, and the weight according to the type and application of the probe P.

For example, the controller 400 may determine the wrist fatigue using Equation 1 below.

$$\text{Total wrist fatigue} = \sum_{j=0}^{m} t_j * f_j \qquad [\text{Equation 1}]$$

Here, j denotes an index number sequentially allocated in the look-up table as shown in FIG. 4 depending on the type and application of a probe P, and $t_j$ denotes the time for which the probe P is used using a specific type and application for a probe P that are selected, and $f_j$ denotes a weight according to the type and application of a probe P.

The value calculated through Equation 1 may be classified according to a preset criterion. That is, the controller 400 may divide the calculated values according to grades that are stored in advance, and may determine the wrist fatigue of the user on the basis of the grades.

In other words, the controller 400 may calculate a numerical value by assigning a weight to a usage time according to the type and application of the probe P of the user, and determine the grade stored in the storage 500 on the basis of the calculated value, thereby predicting the wrist fatigue.

On the other hand, the fatigue grades to which the above described numerical values apply may be variously implemented.

When the wrist fatigue is determined to occur, the controller 400 warns the user about the wrist fatigue through the output 600 (1005).

As described above with reference to FIG. 2, the warning of the user about the wrist fatigue by the ultrasonic diagnostic apparatus 1 according to an example may be output in various forms. When the controller 400 determines that the wrist fatigue does not reach a certain level, the controller 400 may not control the output 600.

Figure 7:
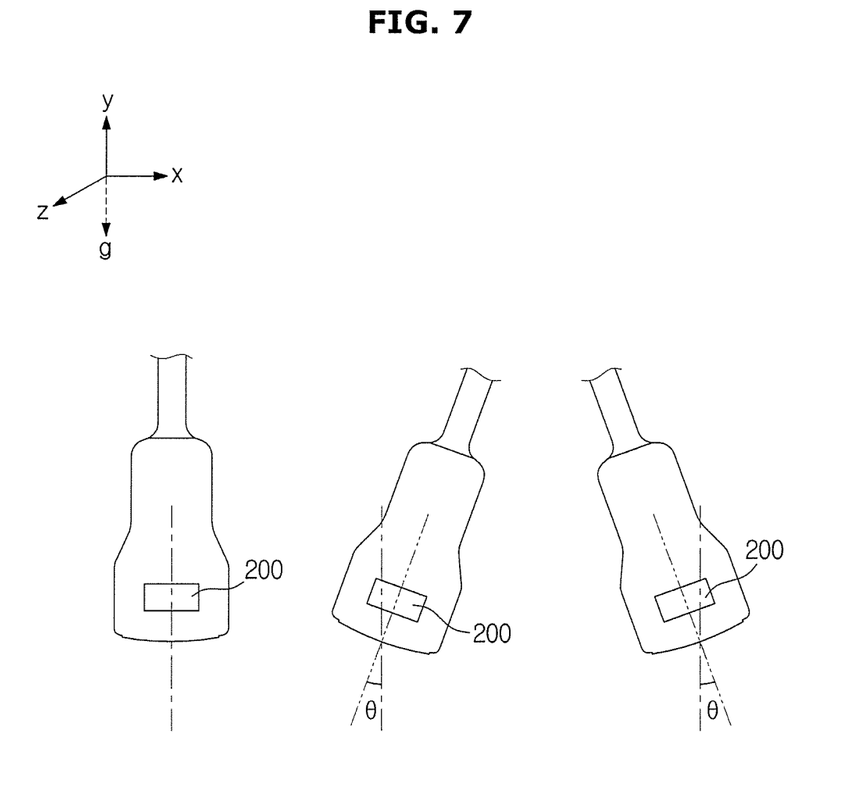
FIG. 7 is a diagram for describing an angle of bend of a wrist using a motion sensor according to another embodiment of the present disclosure.
Figure 8:
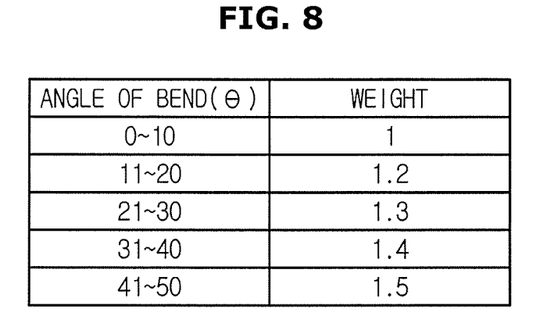
FIG. 8 is a table showing the weights according to the angles of bend.

FIG. 7 is a diagram for describing an angle of bend of a wrist using a motion sensor according to another embodiment of the present disclosure. FIG. 8 is a table showing the weights according to the angles of bend.

Referring to FIG. 7, a probe P according to an embodiment of the present disclosure may include a motion sensor 200.

As described above with reference to FIG. 2, the motion sensor 200 may be a gyro sensor, and measure the angle of bend with respect to a reference direction. In FIG. 7, the three-dimensional space in which the user uses the probe P may be defined by the X, Y, and Z axes. Here, the direction opposite to the Y-axis direction corresponding to the elevating direction is the gravity (g) direction.

The controller 400 may set a reference direction as a direction coinciding with the gravity direction. That is, the position of the probe P arranged first on the left of FIG. 7 may be set as a reference.

Then, when the probe P is moved according to use of the wrist of the user, the controller 400 may determine the angle θ of deviation with respect to the reference direction to be the angle of bend of the wrist.

Although only the angles of bend of the wrist in the X-axis direction are illustrated as in the probe arranged on the second and third order in FIG. 7, the present disclosure is not limited to the X-axis. For example, the angle of bend of the wrist in the Z-axis direction may be measured by the motion sensor 200. In addition, an ascending/descending of the wrist in the Y axis direction, that is, an elevation direction, may be measured.

In the table of FIG. 8, the angle of bend of the wrist may be measured by the motion sensor 200, and the weight represents a weight used for determining the wrist fatigue on the basis of the angle of bend of the wrist.

Referring to the table of FIG. 8, it can be seen that as the angle of bend of the wrist increases, the weight that indicates a wrist fatigue becomes larger. This is based on the assumption that the wrist fatigue becomes greater as the angle of bend of the wrist increases.

Meanwhile, the table shown in FIG. 8 may be stored in the storage 500, and may be used for the controller 400 to determine the wrist fatigue.

Figure 9:
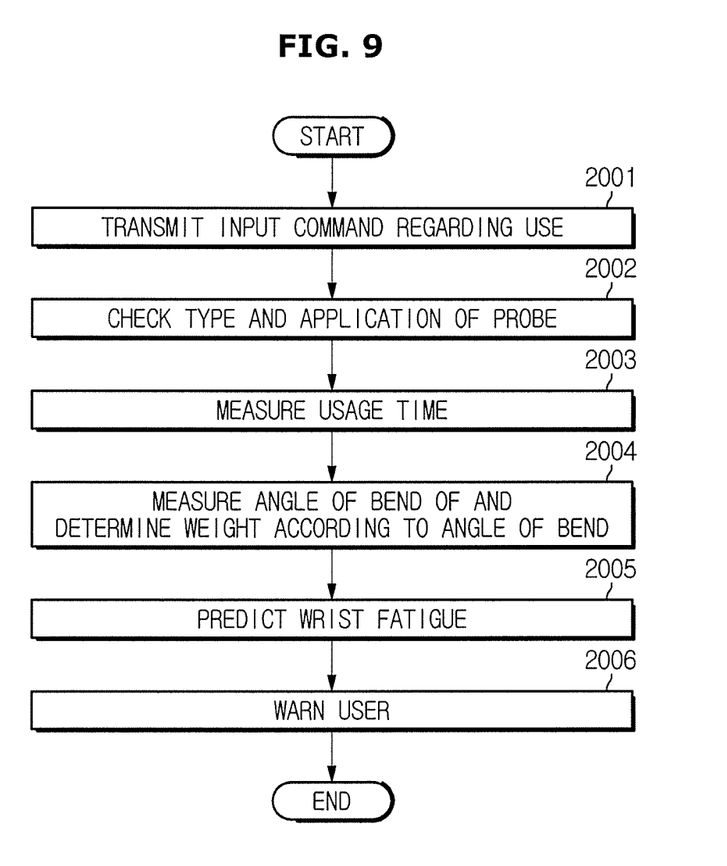
FIG. 9 is a flowchart showing an operation of measuring the angle of bend and determining the wrist fatigue according to another embodiment.

FIG. 9 is a flowchart showing an operation of measuring the angle of bend of the wrist and determining the wrist fatigue according to another embodiment. The same descriptions as those described with reference to FIG. 6 will be omitted.

Referring to FIG. 9, the user transmits information regarding a start of the probe P to the controller 400 through the first input 100 (2001).

Use of the probe P does not need to be continuously performed. Even when the probe P is intermittently used, the controller 400 may accumulate data regarding use of the probe P through the storage 500 and determine the wrist fatigue.

Then, the controller 400 determines the type and application of the probe P through the second input 110 and the like (2002). For the type and application of the probe P, the lookup table described in FIG. 4 may be used.

The controller 400 measures the usage time for which the user uses the probe P (2003).

The controller 400, while measuring the usage time, measures the angle of bend of the probe P according to the usage time. In addition, the controller 400 determines a weight according to the angle of bend of the probe P (2004).

A method of measuring the angle of bend of the probe P using the controller 400 may be the same as the example described with reference to FIG. 7. In addition, the controller 400 may determine the weight that matches the measured angle of bend by referring to the look-up table shown in FIG. 7 stored in the storage 500.

The controller 400 determines the wrist fatigue on the basis of the determined weight and the usage time (2005).

The method of determining the wrist fatigue by the controller 400 may be implemented using the above described Equation 1 together with Equation 2 below. That is, $f_j$ included in Equation 1 for acquiring the wrist fatigue may be calculated by Equation 2.

$$f_j = \text{weight} * \sum_{i=1}^{st} dt * e_i * K \quad \text{[Equation 2]}$$

In Equation 2, st denotes the total sampling interval according to the type and application of the probe P corresponding to index j, weight denotes a weight corresponding to index j, dt denotes a sampling period for motion sensing, and $e_i$ denotes a summation of angular displacements in the X, Y, and Z axes directions during the sampling interval. K is a coefficient for tuning an appropriate amount of displacement.

The angular displacement may be obtained by Equations 3 and 4 below.

$$e_i = A_x e_x + A_y e_y + A_z e_z \quad \text{[Equation 3]}$$

$$e_x = |x_n - x_{n-1}|, e_y = |y_n - y_{n-1}|, e_z = |z_n - z_{n-1}| \quad \text{[Equation 4]}$$

Where, $A_x$, $A_y$ and $A_z$ denote the weights of X, Y, and Z axes. The weights may vary depending on the axis in which a great bending of a wrist occurs. In addition, Xn, Yn, and Zn denote the angles of bend in the X, Y, and Z axes directions measured in the current sampling interval, and Xn-1, Yn-1, and Zn-1 denote the angles of bend in the X, Y, and Z axe directions measured one sampling period ahead of the current sampling period.

After determination of the wrist fatigue, the controller 400 may warn the user about the wrist fatigue through the output 600 as described with reference to FIG. 6 (2006).

For example, the controller 400 may warn the user about the wrist fatigue when the wrist fatigue is determined to be equal to or greater than a reference value. The reference value may vary, and variously implemented according to the numerical values calculated by Equation 1.

Figure 10:
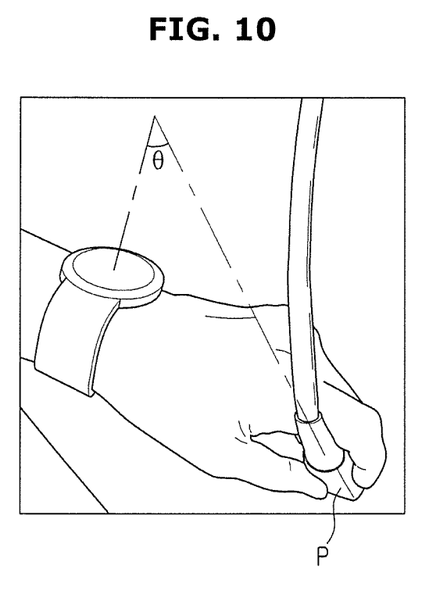
FIG. 10 is a diagram for describing an example in which the wrist fatigue is determined according to another embodiment.

FIG. 10 is a diagram for describing an example in which the wrist fatigue is determined according to another embodiment.

Referring to FIG. 10, a user uses a smartwatch coupled with a motion sensor and a probe P coupled with another motion sensor 200. That is, according to a fatigue measurement with the disclosed embodiment, the wrist fatigue is more accurately determined on the basis of the angle of bend measured using the motion sensor coupled to the smartwatch and the motion sensor 200 coupled to the probe P.

In detail, when the angle of bend of the wrist is measured using only the motion sensor 200 of the probe P, it may be difficult to measure the wrist fatigue accurately because the angle of bend is small. However, when a reference angle of the motion sensor of the smartwatch worn on the user's wrist is used, the angle of bend may be more accurately measured through the distance between the wrist and the probe P.

Accordingly, the controller 400 may set a specific angle of the motion sensor coupled to the smartwatch as a reference, and may measure an angular difference between the angle of the motion sensor 200 coupled to the probe P and the reference.

In detail, the controller 400 may improve the accuracy in measurement of fatigue by applying the measured angular difference between the motion sensors to Equation 5.

In particular, the controller 400 determines $e_i$ of Equation 3 through Equation 5, and substitutes $e_i$ of Equation 3 for Equation 2, finally assigned to Equation 1.

$$e_x = |xX_2 - x_1| + x_{offset}, e_y = |y_2 - y_1| + y_{offset}, e_z = |z_2 - z_1| + z_{offset} \quad \text{[Equation 5]}$$

Where X2 denotes an angle in the X-axis direction obtained from the smartwatch and X1 denotes an angle in the X-axis direction obtained from the probe. $x_{offset}$ denotes a correction value of the X-axis for setting an initial value when the user starts using the probe. This applies also to the Y and Z axes.

That is, $e_i$ is a value obtained from angular differences between the smartwatch and the probe in the X, Y, and Z axes directions. In detail, is a value obtained by calculating an angular difference between the motion sensor of the probe and the motion sensor of the smartwatch in the X axis direction, an angular difference between the motion sensor of the probe and the motion sensor of the smartwatch in the Y axis direction, and an angular difference between the motion sensor of the probe and the motion sensor of the smartwatch in the Z axis direction, and summating the angular differences.

Meanwhile, when the smartwatch is used, the controller 400 may acquire data indicating that the user is using the probe P on the basis of the distance between the probe P and the smartwatch, that is, the signal strength.

In detail, the transmission module 300 of the probe that receives a RF signal generated in the smartwatch determines the signal strength of the received RF signal. The transmission module 300 transmits the received RF signal to the controller 400.

The controller 400 may determine that the user is using the probe P on the basis of the received data. That is, when the RF signal is greater than or equal to a threshold value, the controller 400 may determine that the user is using the probe P without an input of the first input 100.

Although FIG. 10 illustrates a smartwatch as an example of a wearable device, various modification may be possible, such as a band worn on the user's wrist, as long as it can include a motion sensor.

Although not shown in the drawings, the present disclosure may include various modified embodiments. For example, the ultrasonic diagnostic apparatus 1 may determine the wrist fatigue of the user resulting from bending the wrist by using a usage time of the wrist and a measurement value of the angle of bend of the wrist that are transmitted by the wearable device.

In detail, the wearable device measures the angle of bend of the wrist of the user. The angle of bend of the wrist may be measured by a motion sensor installed in the wearable device. The method of determining the angle of bend of the wrist may be implemented using the method described with reference to FIG. 7.

The usage time of the probe P may be measured using an app (APP) installed in the wearable device. For example, when a user executes an app (APP) of a wearable device with a button or a touch, the wearable device may determine the usage time of the APP as the usage time of the probe P. Such an app may be stored in the controller 400 and the storage 500 of the ultrasonic diagnostic apparatus 1 so as to be installed in the wearable device by a user's manipulation.

The controller 400 of the ultrasonic diagnostic apparatus 1 determines the weight on the basis of the usage time of the wrist of the user and the angle of bend of the wrist that are provided by the wearable device. For the weight, the lookup table stored in the storage 500 may be used. That is, the controller 400 may assign different weights according to the input of the user.

The controller 400 may control the output 600 of the ultrasonic diagnostic apparatus 1 according to the determined result of the wrist fatigue and warn the user about the wrist fatigue. In addition, according to the embodiment, the controller 400 may transmit a warning and a display command to the wearable device through the installed app, and control the wearable device so as to warn the user or display an warning.

According to another embodiment of the ultrasonic diagnostic apparatus 1, an app (APP) may be installed in a wearable device and the wrist fatigue of a user may be determined using a motion sensor of the wearable device.

The invention claimed is:

1. An ultrasonic diagnostic apparatus comprising:
a probe including a motion sensor;
a storage configured to store a weight that is determined utilizing a type of the probe or an application of the probe; and
a controller configured to measure an angle of bend of the probe through the motion sensor, and determine a wrist fatigue of a user utilizing the angle of bend of the probe.

2. The ultrasonic diagnostic apparatus of claim 1, wherein the controller determines the wrist fatigue by determining the weights for sampling intervals utilizing the measured angle of bend, stores the usage times with the weights assigned, and summates the usage times.

3. The ultrasonic diagnostic apparatus of claim 1, further comprising an output including at least one of a display, a speaker, or a warning lamp.

4. The ultrasonic diagnostic apparatus of claim 3, wherein the controller controls the output or the probe utilizing the wrist fatigue such that the user is warned.

5. The ultrasonic diagnostic apparatus of claim 4, wherein the controller controls the output or the probe utilizing the wrist fatigue such that the user is warned.

6. The ultrasonic diagnostic apparatus of claim 1, wherein the probe warns the user through vibration.

7. The ultrasonic diagnostic apparatus of claim 6, further comprising an output including at least one of a display, a speaker, or a warning lamp,
wherein the controller controls the output or the probe utilizing the wrist fatigue such that the user is warned.

8. The ultrasonic diagnostic apparatus of claim 1, wherein the controller controls the probe and receives data regarding the usage time and the angle of bend through wireless communication.

9. The ultrasonic diagnostic apparatus of claim 1, wherein the controller measures the angle of bend of the probe by comparing a motion sensor coupled to a wearable device with the motion sensor of the probe.

10. The ultrasonic diagnostic apparatus of claim 9, wherein the wearable device comprises a smart watch worn on a user's wrist.

11. The ultrasonic diagnostic apparatus of claim 9, wherein the controller determines that the probe is used when radio wave signals of the wearable device and the probe have a strength equal to or greater than a threshold value.

12. An ultrasonic diagnostic apparatus comprising:
a probe including a first motion sensor for measuring an angle of bend with respect to a second motion sensor included in a wearable device;
a storage configured to store a weight that is determined utilizing a type of the probe or an application of the probe; and
a controller configured to measure the angle of bend of the probe and determine a wrist fatigue of a user utilizing the angle of bend of the probe,
wherein the angle of bend of the probe is measured utilizing a difference between an angle of the first motion sensor and the second motion sensor in the wearable device.

13. An ultrasonic diagnostic apparatus comprising:
a probe including a motion sensor;
a storage configured to store a weight corresponding to an angle of bend of the probe; and
a controller configured to measure the angle of bend of the probe through the motion sensor, and determine a wrist fatigue of a user utilizing the angle of bend of the probe,
wherein the controller determines the wrist fatigue by applying the weight corresponding to the angle of bend of the probe.

\* \* \* \* \*